United States Patent [19]
Harding

[11] Patent Number: 5,986,754
[45] Date of Patent: Nov. 16, 1999

[54] MEDICAL DIAGNOSTIC APPARATUS USING A FRESNEL REFLECTOR

[75] Inventor: Ian Harding, San Mateo, Calif.

[73] Assignee: Lifescan, Inc., Milpitas, Calif.

[21] Appl. No.: 08/986,560

[22] Filed: Dec. 8, 1997

[51] Int. Cl.[6] .................................................. G01N 21/03
[52] U.S. Cl. ............................................................ 356/246
[58] Field of Search ................................. 356/246, 436, 356/444, 39

[56] References Cited

U.S. PATENT DOCUMENTS

| | | | |
|---|---|---|---|
| D. 375,799 | 11/1996 | Leiva et al. ............................. | D24/224 |
| 4,037,974 | 7/1977 | Fletcher et al. ......................... | 356/246 |
| 4,116,566 | 9/1978 | Sick ........................................ | 356/200 |
| 4,233,029 | 11/1980 | Columbus .............................. | 23/230 R |
| 4,566,791 | 1/1986 | Goldsmith ............................... | 356/246 |
| 5,044,747 | 9/1991 | Anthony ................................. | 356/246 |
| 5,214,277 | 5/1993 | Drennen, III ........................... | 250/216 |
| 5,468,606 | 11/1995 | Bogart et al. ........................... | 435/5 |
| 5,478,527 | 12/1995 | Gustafson et al. ..................... | 422/82.11 |
| 5,522,255 | 6/1996 | Neel et al. .............................. | 73/64.43 |

FOREIGN PATENT DOCUMENTS

WO94/02850 2/1994 WIPO ............................ G01N 33/53

*Primary Examiner*—Richard A. Rosenberger
*Attorney, Agent, or Firm*—James Riesenfeld

[57] ABSTRACT

A device for use in a medical diagnostic apparatus includes an area for containing a sample of biological fluid as it undergoes a reaction that causes a detectable change in the sample's optical properties. The reaction area is sandwiched between a transparent front layer and a Fresnel reflector layer. The area is illuminated through the front layer, and the light is reflected from the reflector layer to a detector. The detector monitors the light incident on it and calculates, from the change during the course of the reaction, an analyte concentration or property of the fluid sample. The reaction area is optionally heated.

7 Claims, 3 Drawing Sheets

MEDICAL DIAGNOSTIC APPARATUS USING A FRESNEL REFLECTOR

BACKGROUND OF THE INVENTION

1. Field of the Invention

This invention relates to a medical diagnostic apparatus for optically measuring the concentration of an analyte in or a property of a biological fluid; more particularly, an apparatus whose optical system includes a Fresnel reflector.

2. Description of the Related Art

A variety of medical diagnostic procedures involve tests on biological fluids, such as blood, urine, or saliva, and are based on a change in light absorption of such a fluid or an element of the fluid, such as blood serum. Some of these procedures make use of a transparent or translucent device to contain the biological fluid and a reagent. A change in light absorption of the fluid can be related to an analyte concentration in, or property of, the fluid. Typically, a light source is located adjacent to one surface of the device and a detector is adjacent to the opposite surface. Alternatively, if a reflector is located adjacent to that opposite surface, then the light can pass through the device twice and the source and detector can be on the same side of the device. A device of this latter type, in which light is first transmitted through the sample area, then reflected through a second time is called a "transflectance" device. References to "light" throughout this specification and the appended claims should be understood to include the infrared and ultraviolet spectra, as well as the visible. References to "absorption" are meant to refer to the reduction in intensity as a light beam passes through a medium, thus, it encompasses both "true" absorption and scattering.

An example of a transparent test device is described in Wells et al. WO94/02850, published on Feb. 3, 1994. Their device comprises a sealed housing, which is transparent or translucent, impervious, and rigid or semi-rigid. An assay material is contained within the housing, together with one or more assay reagents at predetermined sites. The housing is opened and the sample introduced just before conducting the assay. The combination of assay reagents and analyte in the sample results in a change in optical properties, such as color, of selected reagents at the end of the assay. The results can be read visually or with an optical instrument.

U.S. Pat. No. 4,037,974, issued Jul. 26, 1977, to T. Fletcher et al. discloses a sample cell for spectrophotometers, which prevents stray light from being carried to a detector through the cell wall. In one embodiment, the cell has a side wall whose outer surface has a sawtooth configuration, which causes light that enters the side wall from the interior of the cell either to be reflected back into the sample or pass out through the cell wall.

U.S. Pat. No. 4,116,566, issued Sep. 26, 1978, to E. Sick discloses a device for detecting defects in webs of material, using an optical system that may include a sawtooth mirror.

U.S. Pat. No. 4,233,029, issued Nov. 11, 1980, to R. Columbus discloses a liquid transport device that has opposed surfaces, each of which may have a sawtooth cross section. The sawtooth arrangement of one surface is orthogonal to the arrangement of the other surface, and the resultant liquid flow is multidirectional.

U.S. Pat. No. 5,214,277, issued May 25, 1993, to J. Drennen, III discloses a cell that holds near-infrared reflectance spectrometer samples. The spectrometer includes a light source which illuminates a sample that is contained in the cell. The cell surfaces direct the light onto the sample, collect light diffusely reflected from the sample and direct the light back toward a detector.

U.S. Pat. No. 5,522,255, issued Jun. 4, 1996, to G. Neel et al. discloses an instrument and method for determining a coagulation characteristic of blood by a reflectance technique. The sample holder includes a combination reagent heater and reflector. (See also WO95/07452.)

U.S. Pat. No. D 375,799, issued Nov. 19, 1996, to W. Leiva et al. discloses a transparent assay tester for biological fluids with a Fresnel lens.

U.S. Pat. No. 5,468,606, issued Nov. 21, 1995, to G. Bogart et al. discloses an analyte-detecting device which has a substrate with an optically active surface. When illuminated, the surface exhibits different colors, depending on whether or not the analyte is present.

U.S. Pat. No. 5,478,527, issued Dec. 26, 1995, to E. Gustafson et al. discloses a multilayer reflective biograting for use in an immunoassay. The diffraction signal from the biograting changes in the presence of an analyte

SUMMARY OF THE INVENTION

The present invention is a device for use in a medical diagnostic apparatus that comprises a light source to illuminate a sample of a biological fluid and a detector to detect light that has passed through the sample. The device comprises (a) a reaction area for containing at least a portion of the sample, sandwiched between (b) a substantially transparent first layer, and (c) a second layer, which includes a Fresnel reflector, for providing specular reflection of light that has passed through the first layer and the reaction area and directing the light toward the detector.

Another embodiment of the present invention is an apparatus for measuring an analyte concentration or property of a biological fluid comprising (a) a means for illuminating a sample of the biological fluid, (b) means for positioning the sample in the path of light from the illuminating means, (c) means for detecting and measuring light that has interacted with the sample at one or more wavelengths, the detecting and measuring means comprising a Fresnel reflector, and (d) means for calculating the analyte concentration or property of the fluid from the measured reflected light.

As used in the present specification and claims, a "Fresnel reflector" is a reflector having a cross section that is substantially a sawtooth. The reflector may be homogeneous, but preferably it has a reflective coating. An advantage provided by a Fresnel reflector in the present invention is to provide specular, rather than diffuse, reflection of a signal to a detector and thereby to permit a higher signal-to-noise ratio.

Although the "layers" that are elements of the present device are typically thin sheets, that is not necessarily their form, and no thickness limitation is intended by the use of that term.

BRIEF DESCRIPTION OF THE DRAWINGS

FIG. 1A is an enlarged view of a segment of the device of FIG. 1.

DETAILED DESCRIPTION OF THE INVENTION

This invention relates to a diagnostic device for analyzing biological fluid. The device is of the type that contains the fluid to be analyzed in a transparent or translucent container, typically, but not necessarily, a capillary-fill container, and that relates a change in light absorption of the fluid to an analyte concentration in the fluid or to a property of the fluid. The device includes a reaction area, in which the sample undergoes a reaction that causes a change in light absorption; a transparent layer, through which a light beam is incident on the sample; and a second layer, on the side of the sample that is opposite the transparent layer. A Fresnel reflector, at or near a surface of the second layer, reflects light back through the sample and toward a detector.

This type of device is suitable for a variety of analytical tests of biological fluids, such as determining biochemical or hematological characteristics, or measuring the concentration in such fluids of proteins, carbohydrates, lipids, drugs, toxins, gases, electrolytes, etc. The device is particularly well suited for measuring blood clotting time—"prothrombin time" or "PT"—and details regarding such a device appear below. The modifications needed to adapt the device for other applications require no more than routine experimentation.

Figure 1:
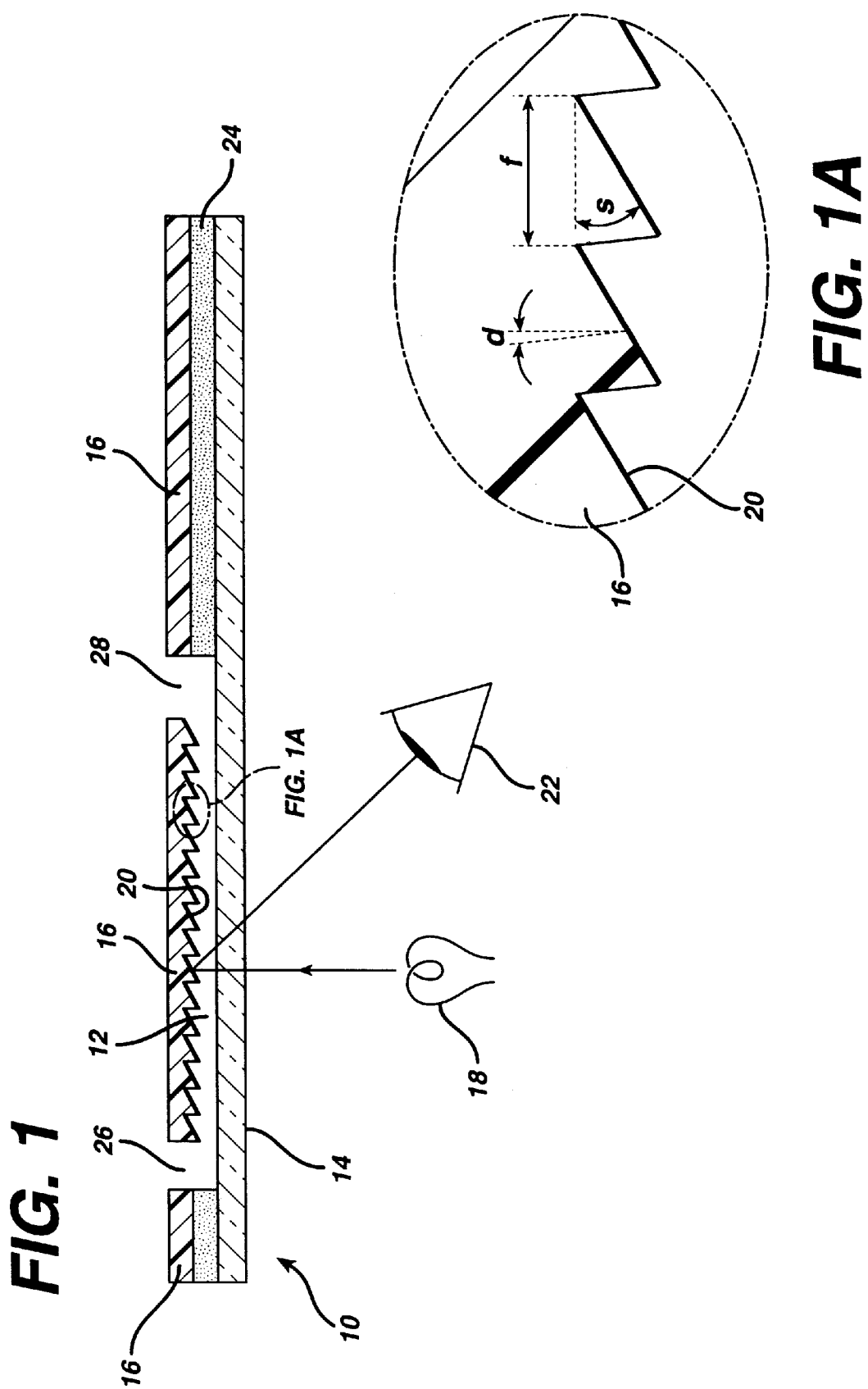
FIG. 1 is a schematic side view of a device of this invention.

FIG. 1 is a schematic of a device 10 of the present invention. Reaction area 12, which for a PT test contains thromboplastin, is sandwiched between transparent layer 14 and backing layer 16. The reaction area is illuminated with light from source 18. After passing through the sample contained in reaction area 12, the light is reflected from Fresnel reflector 20 of backing layer 16 toward detector 22. Optional electrical contacts A and B are discussed below, in connection with the description of FIG. 4. Optional spacer layer 24 separates layers 14 and 16 and has a through hole that forms reaction area 12. Sample (e.g., whole blood or blood plasma, is applied to the reaction area through hole 26 in backing layer 16. In a PT test, thromboplastin in the reaction area reacts with the blood to change the optical properties in a way that can be related to clotting time. The grooved surface of backing layer 16 can form a capillary gap, which, together with optional vent 28, facilitates filling of reaction area 12. Preferably, as shown, reaction area 12 and Fresnel reflector 20 are about the same size, but design considerations, cost, etc. may dictate that one be larger than the other. Similarly, Fresnel reflector 20 may cover part or all of backing layer 16. Transparent layer 14 can be of any suitable transparent material known in the art, such as glass or plastic sheet. Polyester is a preferred material, because it is inexpensive, available, and easy to process. Backing layer 16 may also be of glass or plastic, but it needn't be transparent (if Fresnel reflector 20 adjoins reaction area 12), so it may also be of metal or other non-transparent material. Light source 18 may be an incandescent or fluorescent source of light; preferably, it is one or more LEDs. Detector 22 may be any photodetector that is sensitive to the wavelength(s) of light emitted by source 18. Among the suitable detectors, well known in the art, are photomultiplier tubes, photodiodes, etc. Preferably, detector 22 is a photodiode. Optional spacing layer 24 is preferably double-stick tape, which provides the walls for reaction area 12 and adheres layers 14 and 16 together.

FIG. 1A is an enlarged view of Fresnel reflector 20, which may be the reflective surface of a homogeneous backing layer 16, a reflective coating on the backing layer surface, or a reflective element that is attached to the backing layer. The surface consists of a series of grooves that are characterized by slope angle s, draft angle d, and facet spacing f. Although each of these parameters may change along the length of the reflector, the draft angle and facet spacing are generally constant. The slope angle may change with distance from the optical axis of the reflector, or it can also be constant, depending on whether or not the reflected beam is to be diffused and/or focused. In order to minimize diffraction effects, the facet spacing f should be at least about 10 times the wavelength of light used. Thus, if 900 nm light is used, the facet spacing should be at least 9000 nm, or 9 μm. The facet spacing is preferably not much larger than necessary, since large facet spacing corresponds to a small number of grooves and a thick (in cross section) reflector, neither of which is desirable. The slope angle S is dictated by the parameters of the optical system and the desire to provide specular reflection to the detector. The draft an-le is not critical, since it usually doesn't affect the optical performance of the reflector if it is kept small. Fresnel reflectors and detailed information regarding specific applications are available from Fresnel Optics, Inc., Henrietta, N.Y.

Figure 2:
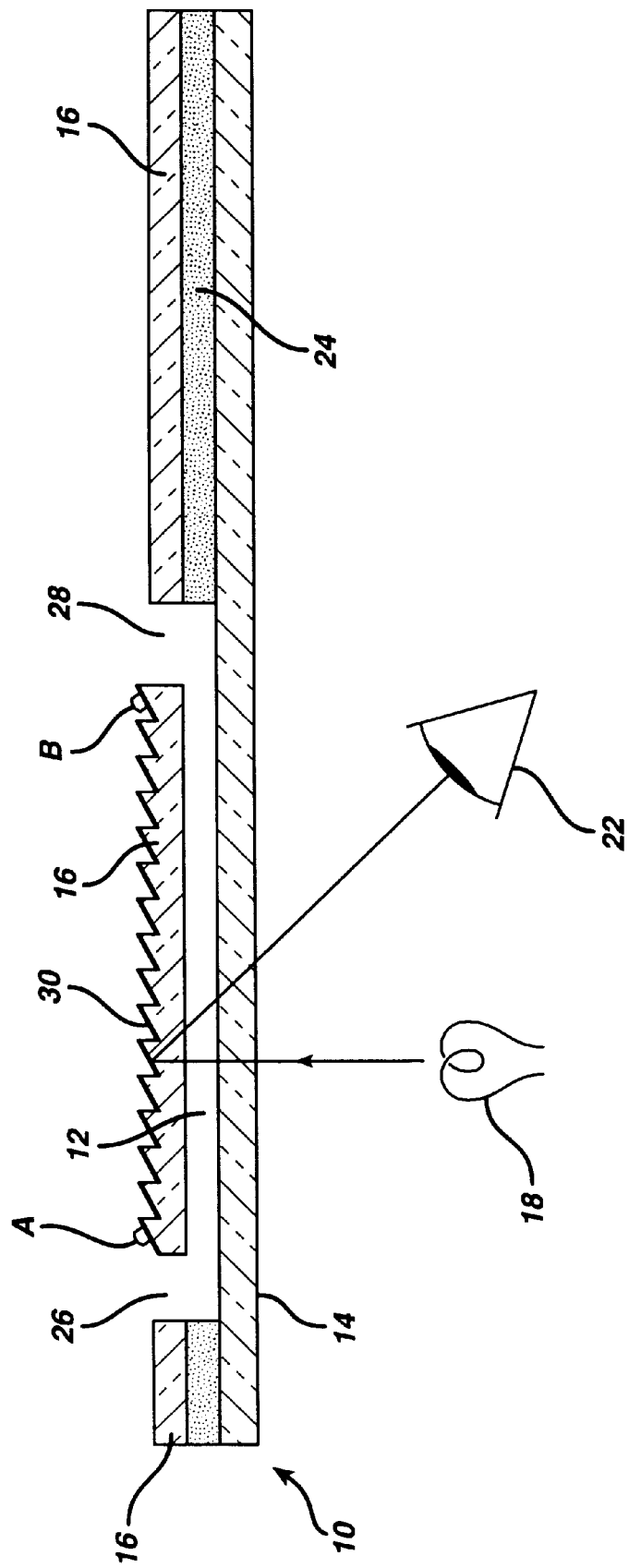
FIG. 2 is a schematic side view of an alternative embodiment of a device of this invention.

The Fresnel reflector in FIGS. 1 and 1A is shown on the "bottom" surface of backing layer 16; i.e., the surface that adjoins the reaction area. As shown in FIG. 2, however, the reflector may be on the top surface 30 of backing layer 16 or it may be sandwiched between two layers that comprise a backing layer. Of course, if the reflector is on the top surface or is sandwiched between two layers, then the layer between the reflector and the reaction area must be transparent. When the Fresnel reflector is on either the top or bottom surface of the backing layer, the backing layer is preferably a metallized transparent sheet.

Figure 3:
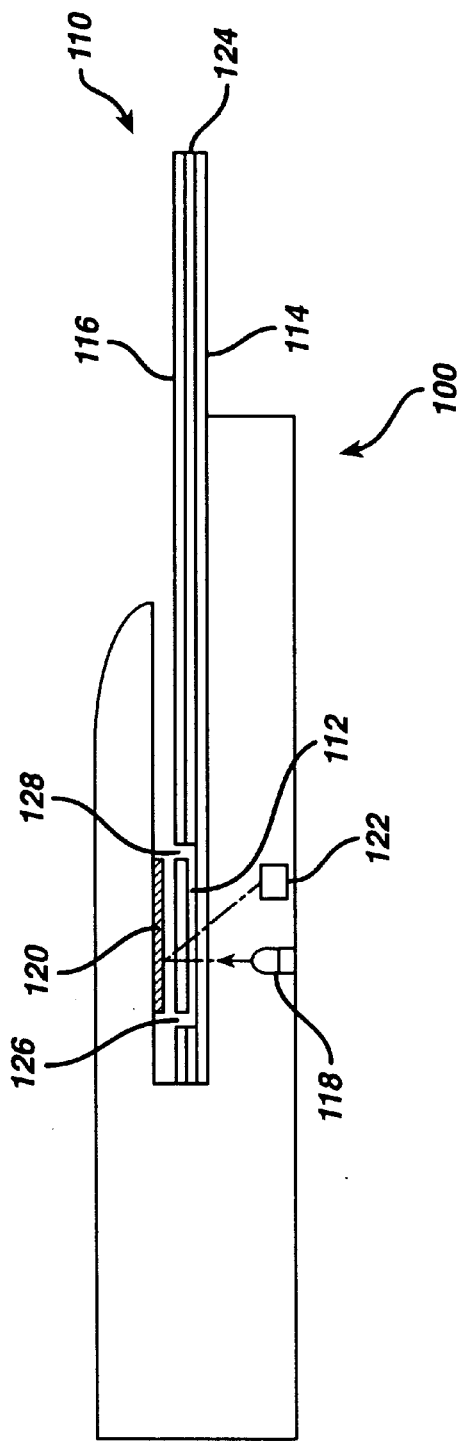
FIG. 3 is a schematic side view of an apparatus of the invention.

FIG. 3 depicts a meter 100 of the present invention. The meter holds a device 110, which has reaction area 112 sandwiched between transparent front layer 114 and transparent backing layer 116. The reaction area is illuminated with light from source 118. After passing through the sample contained in reaction area 112, the light passes through backing layer 116 and is reflected from Fresnel reflector 120 toward detector 122. Optional spacer layer 124 is preferably double-stick tape. The reflected light signal detected by detector 122 is used to calculate the sample property of interest. Preferably, transparent layers 114 and 116 comprise thermoplastic sheets.

Figure 4:
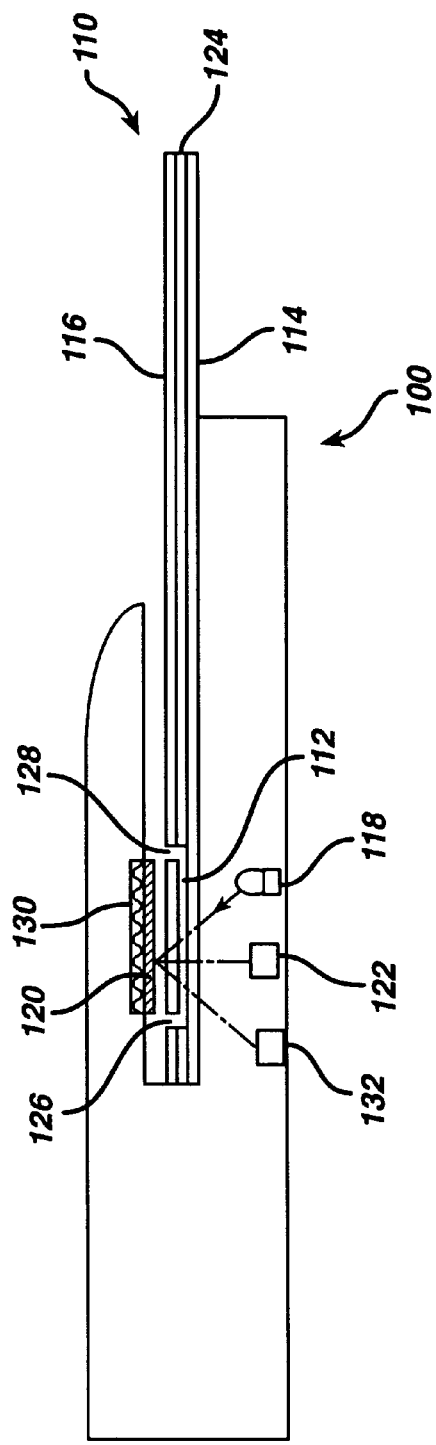
FIG. 4 is a schematic side view of an alternative embodiment of an apparatus of the invention.

FIG. 4 depicts an alternative embodiment of the apparatus of FIG. 3, in which the reaction area is heated with heater 130. Heater 130 may be a radiant heater, resistance heater, or any other suitable type of heater well known in the art. If Fresnel reflector 120 comprises a metallized layer, the layer serves to diffuse the heat, so that the temperature of the reaction area is quite uniform. Alternatively, the metallized layer of device 110 may include electrical contacts (such as A and B shown in FIG. 2), and the reaction layer can be heated by passing a current through the metallized layer. Note that the positions of source 118 and detector 122 are reversed from their positions in FIG. 3. The arrangement in FIG. 4 is preferred when the apparatus is part of an analyzer (such as the "VITROS ECI" Analyzer, available from J&J Ortho Clinical Diagnostics, Rochester, N.Y.) that includes a light source which provides incident light at an acute (e.g., 45°) angle to the plane of the device and a detector that is normal to the plane of the device.

Finally, FIG. 4 includes an optional auxiliary detector 132. The purpose of this detector is to detect gross movement of device 110 during the measurement and to generate an error signal when it detects such gross movement. Detector 132 would normally detect small changes during the course of a measurement. Changes that exceed a threshold value (easily determined by routine experimentation) would trigger the error signal.

I claim:

1. For use in a medical diagnostic apparatus that comprises a light source to illuminate a sample of a biological fluid and a detector to detect light that has passed through the sample, a device that comprises (a) a reaction area for containing at least a portion of the sample, sandwiched between (b) a substantially transparent first layer, and (c) a second layer, comprising a metallized thermoplastic sheet having means for making an electrical connection to the metallized sheet and including a Fresnel reflector, for providing specular reflection of light that has passed through the first layer and the reaction area and directing the light toward the detector.

2. The device of claim 1 in which the biological fluid is whole blood or blood plasma.

3. The device of claim 2 in which the reaction area comprises a reagent that reacts with the blood or plasma to change an optical property thereof in a way that can be quantitatively related to a blood clotting characteristic.

4. The device of claim 1 in which the Fresnel reflector comprises a surface of the second layer that is reflective and that adjoins the reaction area.

5. The device of claim 4 in which the reflective surface is grooved and is spaced apart from an adjoining surface of the first layer a distance that is small enough to maintain a capillary flow of sample into the reaction area when the sample is introduced between the adjoining surfaces.

6. The device of claim 1 in which the Fresnel reflector is separated from the reaction area by a transparent section of the second layer.

7. The device of claim 1 in which the first layer comprises a thermoplastic sheet.

* * * * *